United States Patent
Bisrat et al.

(10) Patent No.: US 6,475,524 B1
(45) Date of Patent: Nov. 5, 2002

(54) COMPOSITION OF MATTER

(75) Inventors: Mikael Bisrat, Strängnäs (SE); Saeed Moshashaee, Stockholm (SE); Håkan Nyqvist, Tullinge (SE); Mustafa Demirbüker, Järfälla (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/486,675
(22) PCT Filed: Nov. 22, 1999
(86) PCT No.: PCT/SE99/02154
§ 371 (c)(1), (2), (4) Date: Mar. 1, 2000
(87) PCT Pub. No.: WO00/30614
PCT Pub. Date: Jun. 2, 2000

(30) Foreign Application Priority Data

Nov. 23, 1998 (SE) .................................................. 9804000

(51) Int. Cl.⁷ .................................................. A61K 9/14
(52) U.S. Cl. ..................... 424/489; 424/45; 424/46; 425/6; 425/7; 265/5; 265/11; 265/12; 265/13; 514/958
(58) Field of Search ............................ 424/489, 45, 46; 514/958; 264/5, 11, 12, 13; 425/6, 7

(56) References Cited

U.S. PATENT DOCUMENTS 5,562,923 A   10/1996   Trofast et al. .............. 424/489
5,851,453 A   12/1998   Hanna et al. .................. 264/5
6,063,138 A * 5/2000   Hanna et al. ............. 23/295 R

FOREIGN PATENT DOCUMENTS

| EP | 0677332 | 10/1995 |
| WO | 9501221 | 1/1995 |
| WO | 9505805 | 3/1995 |
| WO | 9629998 | 10/1996 |
| WO | 9841193 | 9/1998 |

OTHER PUBLICATIONS

Darcy et al., Pharmaceutical Development and Technology, 3(4), 503–507 (1998).

Palakodaty et al., World Congress on Particle Technology 3, 4067–4078 (1998).

* cited by examiner

Primary Examiner—Thurman K. Page
Assistant Examiner—Lakshmi Channavajjala
(74) Attorney, Agent, or Firm—White & Case LLP

(57) ABSTRACT

The invention provides a process for crystallization of amorphous and/or meta-stable crystalline regions of pre-formed particles by treating the particles with a supercritical or subcritical fluid containing an anti-solvent and a solvent. The invention further provides formulations comprising particles produced according to the present process containing one or more pharmacologically active substances and one or more pharmaceutically acceptable excipients, use of said formulations in the treatment of an allergic and/or inflammatory condition of the nose or lungs and methods for treatment of such conditions.

26 Claims, 1 Drawing Sheet

COMPOSITION OF MATTER

FIELD OF THE INVENTION

The present invention is directed to a process for converting amorphous and/or meta-stable crystalline regions of particles into a crystalline state, the resulting particles being useful e.g. for oral or nasal inhalation.

BACKGROUND OF THE INVENTION

The increasing production and use of fine powders in the pharmaceutical industry has high-lighted the need for reliable methods for assessing their physicochemical and technical handling. Particles obtained by spray drying, freeze drying, rapid solvent quenching or from controlled precipitation will often be in an amorphous state and/or in a meta-stable crystalline form. For crystalline substances, a diminution operation, e.g. micronization, will give particles with amorphous regions.

The usefulness of amorphous and/or meta-stable crystalline particles is limited due to their thermodynamic instability. For example, such particles tend to fuse in the presence of moisture, thereby forming hard agglomerates which are difficult to break up. Furthermore, amorphous and/or meta-stable crystalline particles exhibit larger batch-to-batch variations as regards bulk density than do well-defined crystalline particles. This may cause problems e.g. in inhalers for treating respiratory disorders, due to lower dosing accuracy.

It is therefore desirable to convert the amorphous or meta-stable crystalline particles into a crystalline, and therefore, more stable state.

Methods to convert the amorphous or meta-stable crystalline particles into crystalline particles are known. Examples are disclosed in U.S. Pat. No. 5,709,884 and U.S. Pat. No. 5,562,923 both to Astra AB of Sweden.

The known methods to convert amorphous or meta-stable crystalline particles into crystal-line particles are, however, often time consuming requiring substantial space. Therefore, there is a need for a more efficient technique for producing crystalline particles with a high shelf life.

SUMMARY OF THE INVENTION

The object of the present invention is to provide a process for crystallization of amorphous and/or meta-stable crystalline regions of particles e.g. obtained in a preceding micronization stage, comprising treating the particles under supercritical or subcritical conditions with an anti-solvent and a solvent.

According to a preferred embodiment of the invention, the anti-solvent and solvent are carbon dioxide and water, respectively.

According to another preferred embodiment, the relative solvent saturation of the anti-solvent lies in the range of from 15% up to 50% of total solvent saturation at the prevailing pressure and temperature.

DETAILED DESCRIPTION OF THE INVENTION

Figure 1:
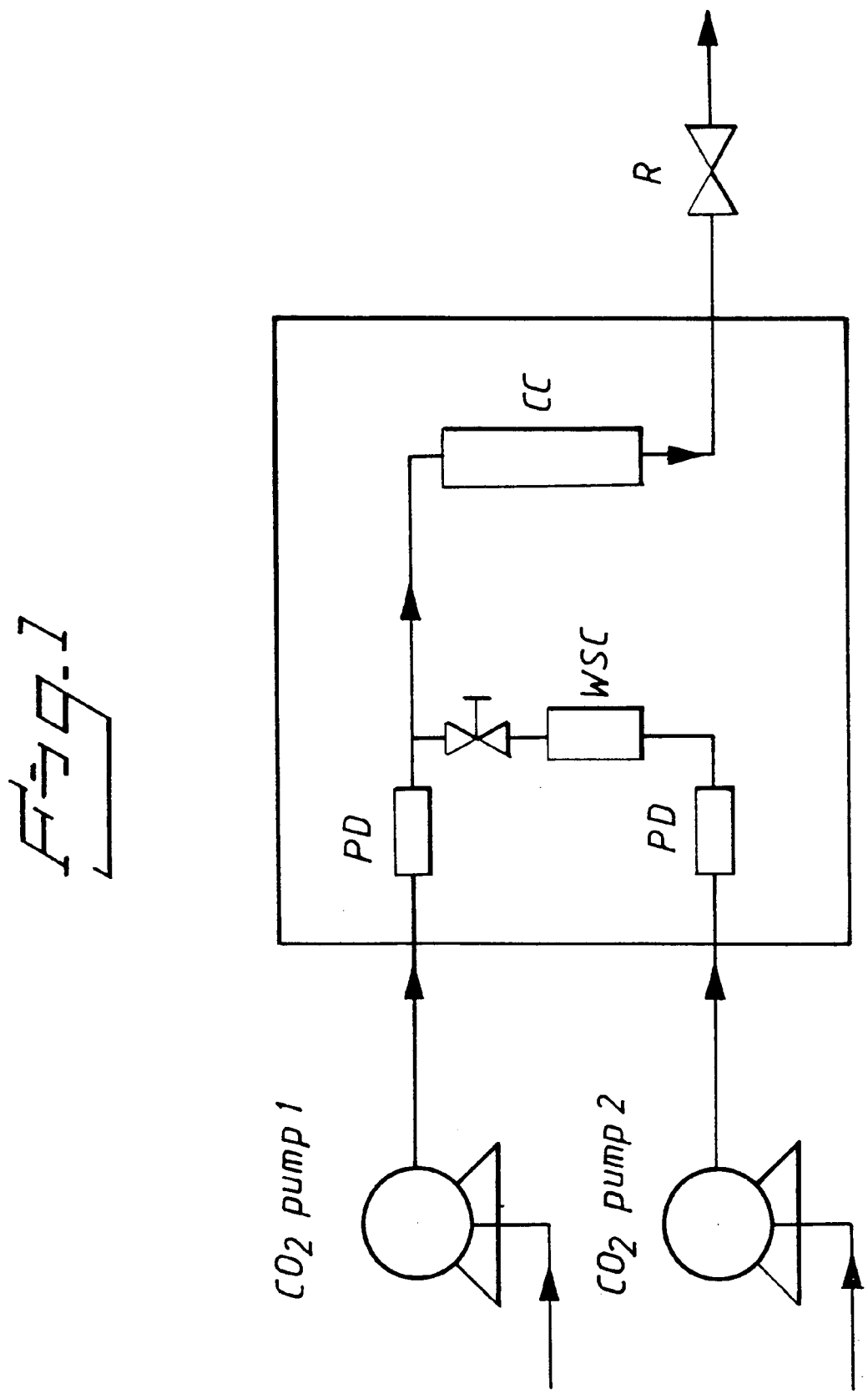
FIG. 1 is a schematic representation of the experimental equipment used for performing the present process.

The present invention relates to a process for converting amorphous and/or meta-stable crystalline regions of preformed particles into an essentially crystalline state, comprising (a) placing the preformed particles in an apparatus suitable for supercritical or subcritical conditions;
(b) treating the particles with a supercritical or subcritical fluid comprising an anti-solvent and a solvent; and
(c) recovering the essentially crystalline particles.

The inventors of the present process, have surprisingly found that the amount of amorphous and/or meta-stable crystalline regions of preformed particles can be reduced considerably while essentially maintaining the size of the particles after applying the process of the invention.

Without being bound by any theory, it can be envisaged that the supercritical or subcritical anti-solvent is an extraordinarily efficient carrier, since under these circumstances the diffusivity becomes very high. In this way, the solvent molecules penetrate quickly and deeply into the amorphous and/or meta-stable crystalline regions of the preformed particles.

The present process therefore, can be applied directly following a procedure where amorphous and/or meta-stable crystalline particles are produced, e.g. in a micronizing, spray-drying or freeze-drying operation.

In the present invention, preformed particles are conditioned without being dissolved in a solvent. Instead, the amorphous and/or meta-stable crystalline regions of the particles are directly transferred into the crystalline state by the influence of the supercritical or sub-critical fluid containing an anti-solvent and a solvent.

A "supercritical fluid" is a fluid at or above its critical pressure ($P_c$) and critical temperature $T_c$) simultaneously. Supercritical fluids also encompass "near supercritical fluids", which are above but close to its critical pressure ($P_c$) and critical temperature $T_c$) simultaneously. A "subcritical fluid" is above its critical pressure ($P_c$) and close to its critical temperature ($T_c$).

The anti-solvent should be selected such that the particle substance at issue is essentially insoluble in the anti-solvent. In this way, the loss of particle substance will be minimized during the present process.

The anti-solvent is suitably one or more of carbon dioxide, nitrous oxide, sulfur hexafluoride, ethane, ethylene, propane, n-pentane, xenon, trifluoromethane, chlorotrifluoromethane, a fluorocarbon compound, a chlorofluorocarbon compound, nitrogen or water. The anti-solvent is preferably carbon dioxide.

In the present invention, the anti-solvent contains a solvent, wherein said solvent is miscible with said anti-solvent. The solvent may be a lower alkyl alcohol, such as methanol, ethanol, n-propanol, isopropanol, n-butanol, isobutanol, sec-butanol or tert-butanol, an aldehyde, a ketone, an ester, a base such as ammonia or pyridine, or any mixture of any of these, as long as the mixture of anti-solvent and solvent is in one and only one phase when contacted with the particles. The solvent is suitably a polar solvent, preferably water.

Immediately before treating the particles in the conditioning vessel, the relative solvent saturation of the anti-solvent may be in the range of from about 1% up to 100%, i.e. total, solvent saturation at the prevailing pressure and temperature. Immediately before treating the particles in the conditioning vessel, the relative solvent saturation of the anti-solvent is suitably in the range of from 15% up to 50%, preferably from 20% up to 45%, and more preferably from 25% up to 40% of total solvent saturation at the prevailing pressure and temperature.

A particularly preferred combination of anti-solvent and solvent is carbon dioxide and water, advantageously when the relative water-saturated supercritical carbon dioxide (RWSSC) lies in the range from about 20% up to about 40%, and especially when the RWSSC lies in the range from 25% up to 35% of total solvent saturation at the prevailing pressure and temperature.

A suitable relative solvent saturation may be obtained by pumping dry and totally solvent-saturated anti-solvent at suitable flow rates through a tee-piece such that they are completely mixed before reaching the conditioning vessel containing the particles with amorphous and/or meta-stable crystalline regions. When the pressure and temperature of the dry and totally solvent-saturated anti-solvent are identical, the flow-rate ratio determines the resulting relative solvent saturation.

The flow-rate ratio between dry and totally solvent saturated anti-solvent may be in the range of from about 10:1 to about 1:10, suitably from 8:1 to 1:5, preferably from 6:1 to 1:1, when preparing a supercritical or subcritical fluid which is not totally solvent saturated.

The essentially crystalline, preferably totally crystalline, particles produced according to the present process, may be subsequently treated with a dry anti-solvent in a supercritical or subcritical state for avoiding precipitation of the solvent upon pressure reduction and for obtaining particularly dry particles. Preferably, the anti-solvent containing a solvent and the dry anti-solvent are both carbon dioxide.

The particles of the invention may contain one or more pharmacologically active substance(s) and/or one or more pharmaceutically acceptable excipients, both intended for use in mammals, preferably human beings.

Pharmaceutically acceptable excipients are e.g. carriers, additives and diluents, including antioxidants. Suitable pharmaceutically acceptable excipients include, without limitation, one or more natural or synthetic carbohydrates, such as monosaccharides, disaccharides, trisaccharides, oligosaccharides, polysaccharides and polyols, and/or in the form of their pharmaceutically acceptable esters, acetals, salts or solvates thereof (where such derivatives exist). When the carbohydrate is in a solvated form it is suitably a hydrate, such as a monohydrate, dihydrate or trihydrate. Examples of naturally occurring monosaccharides include glucose, fructose and galactose. Examples of naturally occurring disaccharides include sucrose (saccharose), trehalose, maltose, cellobiose and lactose. The disaccharide is preferably lactose, more preferably lactose monohydrate. Examples of naturally occurring trisaccharides include raffinose and melezitose. The polysaccharide may be cellulose, starch, dextrins or dextran, or chemical derivatives of any of these. The cellulose derivative is suitably a cellulose ether such as ethylcellulose (EC), ethylmethylcellulose (EMC), hydroxyethylcellulose (HEC), ethylhydroxymethylcellulose (EHMC), ethylhydroxyethylcellulose (EHEC), methylcellulose (MC), hydroxymethylcellulose (HMC), hydroxypropylcellulose (HPC), hydroxypropylmethylcellulose (HPMC) and carboxymethylcellulose (CMC), e.g. the sodium salt thereof. The polyol is preferably a sugar alcohol, which can be obtained by reducing various monosaccharides. For example, sorbitol and mannitol may be obtained by reducing glucose and mannose, respectively.

Pharmacologically active substances for use in the present invention can be selected from the group consisting of β agonists, including short acting and long acting β1 and β2 agonists, glucocorticosteroids, anticholinergics, leukotriene antagonists, and proteins and peptides, especially inhalable proteins and peptides, and any mixture thereof β agonists for use in the present invention include, without limitation, formoterol, salbutamol, rimiterol, fenoterol, reproterol, pirbuterol, bitolterol, salmeterol, clenbuterol, procaterol, broxaterol, picumeterol, mabuterol, terbutaline, isoprenaline, orciprenaline, adrenaline, and pharmaceutically acceptable esters, acetals, salts and solvates thereof, solvates of any of these (where such derivatives exist), and any mixture thereof.

The glucocorticosteroid, if used in the invention, is preferably an anti-inflammatory glucocorticosteroid, e.g. for use in nasal or oral inhalation, or for use in the treatment of intestinal diseases such as inflammatory bowel diseases (IBD), Crohn's disease or ulcerative colitis. Examples of glucocorticosteroids which may be used in the present invention include betamethasone, fluticasone (e.g. as propionate), budesonide, tipredane, dexamethasone, beclomethasone (e.g. as dipropionate), prednisolone, fluocinolone (e.g. as acetonide), triamcinolone (e.g. as acetonide), mometasone (e.g. as furoate), rofleponide, flumethasone, flunisolide, ciclesonide, deflazacort, cortivazol, $16\alpha$, $17\alpha$-butylidenedioxy-$6\alpha,9\alpha$-difluoro-$11\beta$, 21-dihydroxy-pregna-1,4-diene-3,20-dione; $6\alpha,9\alpha$-difluoro-$11\beta$-hydroxy-$16\alpha$, $17\alpha$-butylidenedioxy-$17\beta$-methylthio-androsta-4-ene-3-one; $16\alpha,17\alpha$-butylidenedioxy-$6\alpha,9\alpha$-difluoro-$11\beta$-hydroxy-3-oxo-androsta-1,4-diene-$17\beta$-carbothioic acid S-methyl ester; methyl $9\alpha$-chloro-$6\alpha$-fluoro-$11\beta$-hydroxy-$16\alpha$-methyl-3-oxo-$17\alpha$-propionyloxy-androsta-1,4-diene-$17\alpha$-carboxylate; $6\alpha,9\alpha$-difluoro-$11\beta$-hydroxy-$16\alpha$-methyl-3-oxo-$17\alpha$-propionyloxy-androsta-1,4-diene-$17\beta$-carbothioic acid S-(2-oxo-tetrahydrofuran-3-yl) ester; optionally in their pure isomeric forms (where such forms exist) and/or in the form of their pharmaceutically acceptable esters, acetals or salts, where applicable, and solvates thereof. Suitably, use is made of mometasone furoate, beclomethasone dipropionate or fluticasone propionate or glucocorticosteroids with an asymmetric acetal structure, e.g. comprising $16\alpha,17\alpha$-butylidenedioxy group, such as budesonide or rofleponide as solvates where such exist.

The preformed particles of the present invention may contain pharmacologically active substance or substances premixed with one or more pharmaceutically acceptable excipients before the process of the invention is applied. This is especially advantageous if the active substance is highly potent or if the active substance is formulated with an external layer of excipients for controlled release. It is, however, also possible to prepare crystalline particles containing an active substance according to the present invention and mix them with suitable excipient(s) afterwards. In this case, the excipient particles may also be produced according to the present invention, or may be produced by some other suitable technique. It is further possible to prepare crystalline particles containing one or more excipient(s) according to the present invention and mix them with particles containing one or more active substances afterwards. In this case, the particles containing an active substance may also be produced according to the present invention, or may be produced by some other suitable technique.

The degree of crystallinity can be measured using various analytical techniques. Isothermal microcalorimetry is a sensitive analytical technique which can be used advantageously as a measure of crystallinity. The technique determines the energy content of the particles by measuring the heat given off by amorphous and/or meta-stable crystalline regions during crystallization when the particles are subjected to a solvent-containing, normally water-containing, atmosphere. The TAM value is obtained using a Thermal Activity Monitor 2277 apparatus (Thermometrics AB, Sweden). Reference is made to Buckton, G. and Darcy, P., Int. J. Pharmaceutics, 123 (1995), pp. 265–271 and U.S. Pat. No. 5,709,884 to Astra AB, especially col. 5–6.

With the present process, it is possible to drastically reduce the energy content of the particles and therefore also the TAM value. Thus, the TAM value for the particles measured before and after the conditioning step may be reduced by a factor of more than 5, suitably more than 10, more suitably more than $10^2$, and preferably by a factor of more than $10_3$.

More particularly, with the present process it is possible to produce and recover essentially crystalline compounds according to the invention with a TAM value of less than about 3 J/g, suitably less than 1 J/g, and preferably less than 0.5 J/g. One typical example is lactose monohydrate giving a TAM value of 0.1–1 J/g (see Example, Table 3).

Generally, the particles produced may have a particle size of less than about 500 μm, suitably less than 200 μm, and preferably with an MMD in the range of from 1 to 80 μm.

When the particles produced contain a pharmacologically active substance the particles are suitably in a finely divided form, preferably having a mass median diameter (MMD) (as measured using a Coulter counter) of less than about 20 μm, more preferably of less than 10 μm, and most preferably with an MMD in the range of from 1 to 6 μm. The particles may alternatively be in an ultra fine form, e.g. having an MMD of less than 1.0 μm.

When the particles produced contain one or more pharmaceutically acceptable excipients the particles may have a mass median diameter (MMD) (as measured using a Coulter counter) of less than about 100 μm, suitably of less than 50 μm, preferably with an MMD of less than 20 μm, and more preferably with an MMD of less than 10 μm.

Finely divided particles, i.e. essentially particles having an MMD of less than about 10 μm, may be produced by conventional techniques known per se, e.g. by micronization or by direct precipitation. Information about micronization can be found e.g. in "The Theory and Practice of Industrial Pharmacy", Lachman, Liebermann and Klang, $2^{nd}$ Ed., 1976, Lea & Febiger, Philadelphia, USA.

The present process is carried out under supercritical or subcritical conditions. The precise conditions of operation are dependent e.g. upon the choice of anti-solvent. It is, however, desirable that the combination of pressure and temperature is selected such that the particles essentially maintain their chemical purity and physical form after the conditioning step. Table 1, lists the critical pressure ($P_c$) and critical temperature ($T_c$) for some anti-solvents.

TABLE 1

| Anti-solvent | $P_c$ (bar) | $T_c$ (° C.) |
| --- | --- | --- |
| Carbon dioxide | 74 | 31 |
| Nitrous oxide | 72 | 36 |
| Sulfur hexafluoride | 37 | 45 |
| Ethane | 48 | 32 |
| Ethylene | 51 | 10 |
| Xenon | 58 | 16 |
| Trifluoromethane | 47 | 26 |
| Chlorotrifluoromethane | 39 | 29 |

In practice, it may be preferable to maintain the pressure inside the conditioning vessel substantially above the relevant $P_c$ whilst the temperature is only slightly above the $T_c$. Generally, therefore, the pressure may be in the range of from about 10 up to about 300 bar higher than the relevant $P_c$, suitably in the range of from 20 up to 200 bar higher, and preferably be in the range of from 30 up to 100 bar higher than the relevant $P_c$. Generally, also, the temperature may be in the range of from about 5 up to about 50° C. above the relevant $T_c$, suitably in the range of from 10 up to 40° C. above, and preferably in the range of from 15 up to 30° C. above the relevant $T_c$.

With carbon dioxide, the pressure may be in the range of from about 80 up to about 400 bar, suitably in the range of from 100 to 250 bar, preferably in the range of from 110 to 150 bar whilst the temperature may be in the range of from about 35 up to about 80° C., suitably in the range of from 40 up to 70° C., preferably in the range of from 45 up to 60° C.

The supercritical or subcritical fluid containing an antisolvent and a solvent should be pumped through the conditioning vessel for a period of time selected such that the desired particle characteristics are obtained. The period of time can be regulated by altering the pressure, temperature and/or flow rate. The supercritical or subcritical fluid containing an anti-solvent and a solvent can be pumped for a period of time in the range of from about 5 min up to about 48 hours, suitably from 15 min up to 24 hours, preferably from 30 min up to 12 hours.

Conveniently, the present process is carried out as a one-way process, i.e. the supercritical or subcritical fluid passes the conditioning vessel only once. It is, however, possible to recirculate the supercritical or subcritical fluid after essentially restoring the initial relative or total solvent saturation value before the fluid reenters the conditioning vessel.

An apparatus suitable for use as a conditioning vessel in the present process, must be able to withstand the pressure and temperature prevailing at the preselected supercritical or subcritical condition. Furthermore, the apparatus must be able to with-stand the impact of the anti-solvent/solvent mixture at issue under supercritical or subcritical conditions.

According to the invention there is also provided a pharmaceutical formulation comprising one or more pharmacologically active substances and one or more pharmaceutically acceptable excipients at least one of which produced according to the present invention. Examples of such excipients include carriers such as carbohydrates e.g. in a solvated form, additives such as antioxidants, and diluents. The active substance(s) are preferably selected from the group consisting of β agonists, glucocorticosteroids, anticholinergics, leukotriene antagonists, proteins and peptides, and any mixture thereof.

The invention further provides formulations produced according to the present process containing one or more pharmacologically active substance(s) selected from the group consisting of β agonists, glucocorticosteroids, anticholinergics, leukotriene antagonists, proteins and peptides, mixed with one or more pharmaceutically acceptable excipient(s), for use in the treatment of a respiratory disorder such as an allergic and/or inflammatory condition of the nose or lungs, e.g. chronic obstructive pulmonary disease (COPD), rhinitis or asthma, or for use in the treatment of intestinal diseases such as inflammatory bowel diseases (IBD), Crohn's disease or ulcerative colitis.

The invention further provides a method for treatment of an allergic and/or inflammatory condition of the nose or lungs by administering to a mammal, especially a human being, suffering from such a condition a therapeutically effective amount of a formulation containing one or more pharmacologically active substance(s) selected from β agonists, glucocorticosteroids, anticholinergics, leukotriene antagonists, proteins and peptides, mixed with one or more pharmaceutically acceptable excipient(s). More specifically, the invention provides a method for treatment of chronic obstructive pulmonary disease (COPD), rhinitis, asthma or other allergic and/or inflammatory conditions, or for treatment of intestinal diseases such as inflammatory bowel diseases (IBD), Crohn's disease or ulcerative colitis by administering to a mammal, especially a human being, suffering from such a condition a therapeutically effective amount of a formulation containing one or more pharmacologically active substance(s) selected from β agonists, glucocorticosteroids, anti-cholinergics, leukotriene antagonists, proteins and peptides, mixed with one or more pharmaceutically acceptable excipient(s).

The invention will be illustrated by the following example which is not intended to limit the scope of the invention.

EXAMPLE

Experiments were performed according to the invention in the equipment shown in FIG. 1, wherein carbon dioxide with a relative water-saturation in the range of from 20 to 40% was used for crystallizing amorphous lactose monohydrate.

A conditioning vessel (CC, Keystone SFE) with a volume of 50 ml was packed with 400–500 mg of amorphous lactose monohydrate.

Dry supercritical carbon dioxide was pumped through the conditioning vessel using $CO_2$ pump 1 until the desired pressure was reached.

Supercritical carbon dioxide totally saturated with water vapor was prepared by passing dry supercritical carbon dioxide (using a $CO_2$ pump 2) through a water-saturation vessel (WSC, Keystone SFE) used as a water reservoir. The water-saturation vessel was filled with a bed of chemical clean filter paper and 1–3 ml of water was poured into the paper bed.

Both the water-saturation vessel (WSC) and the conditioning vessel (CC) were placed vertically in the oven (shown as a square) where the temperature was controlled.

The pressure inside the water-saturation and conditioning vessels was regulated using a common back pressure regulator (R) from Jasco, Japan. Pulse dampeners (PD) were used to reduce the pressure fluctuations in the equipment.

Once the system reached steady state with respect to the temperature and pressure, the dry supercritical carbon dioxide was mixed with the supercritical carbon dioxide totally saturated with water vapor, i.e. carbon dioxide where the relative water-saturated super-critical carbon dioxide (RWSSC) was 0% and 100%, respectively. In this way, desirable relative water-saturated supercritical carbon dioxide (RWSSC) was obtained for conditioning the amorphous lactose monohydrate inside the conditioning vessel.

After conditioning the lactose monohydrate sample for 2 hours, the system was depressurized. The conditioned lactose monohydrate was collected, weighed and analyzed.

Between the test runs, the conditioning vessel was rinsed with 1–1.5 vessel volumes of dry carbon dioxide.

TABLE 2

Working conditions used for conditioning of amorphous lactose monohydrate

| Batch no | Pressure (bar) | Temperature (° C.) | $CO_2$ flow rate ratio (dry: totally sat.) | RWSSC (%) |
|---|---|---|---|---|
| 1 | 120 | 40 | 16:4 | 20 |
| 2 | 120 | 40 | 14:6 | 30 |
| 3 | 120 | 70 | 12:8 | 40 |
| 4 | 120 | 40 | 12:8 | 40 |

The physical characteristics of each sample following the treatment according to the invention are shown in Table 3.

The characteristics of an untreated sample is shown for comparison (Batch No. 0).

Dv90 is a measure of the particle size. Dv90 means that 90% of the particles have a size smaller than the size at issue.

Dv(90-10) is a measure of the particle size distribution. Dv(90-10) is the difference between Dv90 and Dv10 (10% of the particles have a size smaller than the size at issue).

The particle size and particle size distribution for each sample was measured as the mass median diameter (MMD), Dv90 and Dv(90-10) using a Coulter counter.

TABLE 3

Characteristics of lactose monohydrate treated according to the invention

| Batch No. | MMD (μm) | Dv90 | Dv(90-10) | TAM (J/g) |
|---|---|---|---|---|
| 0 | 2.7 | — | 3.5 | 9.4 |
| 1 | 2.7 | 4.8 | 3.5 | 1 |
| 2 | 2.7 | 4.9 | 3.6 | 0.5 |
| 3 | 2.7 | 4.9 | 3.6 | 0.4 |
| 4 | 5.48 | 17.2 | — | 0.1 |

As is evident from Table 3, the batches treated according to the present invention (Batch No. 1–4) have a lower TAM value, i.e. higher crystallinity, than the untreated sample (Batch No. 0).

What is claimed is:

1. A process for the preparation of essentially crystalline particles, comprising:
   (a) placing preformed particles having amorphous and/or meta-stable crystalline regions in an apparatus suitable for supercritical or subcritical conditions; and
   (b) treating the particles with a supercritical or subcritical fluid comprising an anti-solvent and a solvent to form the essentially crystalline particles.

2. The process according to claim 1, wherein the anti-solvent is carbon dioxide.

3. The process according to claim 1, wherein the process is conducted at a temperature in the range of from about 5 up to about 50° C. above the critical temperature ($T_c$) of the anti-solvent.

4. The process according to any previous claim, wherein the process is conducted at a pressure in the range of from about 10 up to about 300 bar higher than the critical pressure ($P_c$) of the anti-solvent.

5. The process according to claim 1, wherein the solvent is a polar solvent.

6. The process according to claim 5, wherein the polar solvent is water.

7. The process according to claim 1, wherein before treating the particles the supercritical or subcritical fluid is saturated with the solvent in the range of from 15% up to 50% of total solvent-saturation at the prevailing pressure and temperature.

8. The process according to claim 1, wherein the particles comprise one or more pharmaceutically acceptable carbohydrates selected from the group consisting of monosaccharides, disaccharides, trisaccharides, oligosaccharides, polysaccharides and polyols, and any esters, acetals, salts or solvates thereof.

9. The process according to claim 8, wherein the disaccharide is lactose monohydrate.

10. The process according to claim 8 or 9, wherein the particles containing a carbohydrate have a mass median diameter (MMD) of less than about 100 μm.

11. The process according to claim 1, wherein the particles have a thermal activity monitor (TAM) value after step (c) of less than 3 J/g.

12. The process according to claim 11, wherein the TAM value for the particles measured before step (a) and after step (c) is reduced by a factor of more than 5.

13. The process according to claim 9, wherein the lactose monohydrate particles have a thermal activity monitor (TAM) value after step (c) of less than 1 J/g.

14. The process according to claim 1, wherein the particles comprise one or more pharmacologically active substance(s) selected from the group consisting of β agonists, glucocorticosteroids, anticholinergics, leukotriene antagonists, proteins and peptides, and any mixture thereof.

15. The process according to claim 14, wherein the particles containing one or more pharmacologically active substance(s) have a mass median diameter (MMD) of less than 10 μm.

16. The process according to claim 1, comprising treating the particles from step(b) with a supercritical or subcritical fluid comprising a dry anti-solvent, before recovering the essentially crystalline particles.

17. The process according to claim 16, wherein the dry anti-solvent is carbon dioxide.

18. The process according to claim 1, wherein the process is conducted at a temperature in the range of from 15 up to 30° C. above the critical temperature ($T_c$) of the anti-solvent.

19. The process according to any one of claims 1–3 or 18, wherein the process is conducted at a pressure in the range of from about 30 up to about 100 bar higher than the critical pressure ($P_c$) of the anti-solvent.

20. The process according to claim 1, wherein before treating the particles the supercritical or subcritical fluid is saturated with the solvent in the range of from 25% up to 40% of total solvent-saturation at the prevailing pressure and temperature.

21. The process according to claim 8 or 9, wherein the particles containing a carbohydrate have a mass median diameter (MMD) of less than 10 μm.

22. The process according to claim 1, wherein the particles have a thermal activity monitor (TAM) value after step (c) of less than 1 J/g.

23. The process according to claim 1, wherein the particles have a thermal activity monitor (TAM) value after step (c) of less than 0.5 J/g.

24. The process according to claim 11, wherein the thermal activity monitor (TAM) value for the particles measured before step (a) and after step (c) is reduced by a factor of more than $10^2$.

25. The process according to claim 14, wherein the particles containing one or more pharmacologically active substance(s) have a mass median diameter in the range of from 1 to 6 μm.

26. The process according to claim 9, wherein the lactose monohydrate particles have a thermal activity monitor (TAM) value after step (c) of less than 0.1 J/g.

* * * * *